(12) United States Patent
Frauens

(10) Patent No.: US 10,258,473 B2
(45) Date of Patent: Apr. 16, 2019

(54) DEVICE AND METHOD FOR RESTORING JOINTS WITH ARTIFICIAL CARTILAGE

(75) Inventor: John T. Frauens, Honolulu, HI (US)

(73) Assignee: SoftJoint Corporation, Honolulu, HI (US)

( * ) Notice: Subject to any disclaimer, the term of this patent is extended or adjusted under 35 U.S.C. 154(b) by 594 days.

(21) Appl. No.: 12/273,812

(22) Filed: Nov. 19, 2008

(65) Prior Publication Data

US 2010/0125341 A1    May 20, 2010

(51) Int. Cl.
*A61F 2/28* (2006.01)
*A61F 2/30* (2006.01)

(52) U.S. Cl.
CPC ............ *A61F 2/30756* (2013.01); *A61F 2002/30069* (2013.01); *A61F 2002/30075* (2013.01); *A61F 2002/30757* (2013.01); *A61F 2210/0061* (2013.01)

(58) Field of Classification Search
CPC .............. A61F 2002/30757; A61F 2002/2828
USPC ......... 623/14.12, 18.11, 23.11–23.14, 23.42, 623/23.6
See application file for complete search history.

(56) References Cited

U.S. PATENT DOCUMENTS

| | | | |
|---|---|---|---|
| 3,053,251 A * | 9/1962 | Black et al. ............... | 623/23.12 |
| 3,252,943 A | 5/1966 | Dankert et al. | |
| 3,867,350 A | 2/1975 | Pedain et al. | |

(Continued)

FOREIGN PATENT DOCUMENTS

| | | |
|---|---|---|
| DE | 2501080 A1 | 7/1976 |
| DE | 20003360 U1 | 6/2001 |

(Continued)

OTHER PUBLICATIONS

DSM Biomedical Inc., "Bionate: Thermoplastic Polycarbonate Polyurethane (PCU)", Accessed on Oct. 10, 2014 via http://www.dsm.com/content/dam/dsm/medical/en_US/documents/bionate(r)-pcu-product-sheet.pdf, Copyright 2012, pp. 1-4.

(Continued)

*Primary Examiner* — Megan Y Wolf
(74) *Attorney, Agent, or Firm* — Steven J. Hultquist; Hultquist, PLLC

(57) ABSTRACT

An intra-articular device comprises a membrane shaped like a cap having a peripheral geometry similar to that of a head of a bone for a joint to be restored and an open end sized to be applied over the bone proximate the head, so that the open end can be stretched over the head of the bone and held in position on the bone interposed between the head and its corresponding articular component of the joint. The membrane is made of a polyether-urethane-urea material selected to have a property of absorbing the joint's own synovial fluid so as to swell and have a viscoelastic property similar to the body's own articular hyaline cartilage. In a preferred embodiment, the membrane cap is adapted for use on a femoral bone for restoring a hip joint. A related method of installing an intra-articular device as artificial cartilage comprises forming a membrane cap to be applied over the head of the bone of the joint, surgically exposing the head of the bone, installing the membrane cap over the head of the bone, then repositioning the capped head of the bone back in its place in the joint with the membrane interposed as artificial cartilage.

2 Claims, 5 Drawing Sheets

(56) References Cited

U.S. PATENT DOCUMENTS

| | | |
|---|---|---|
| 4,576,718 A | 3/1986 | Reischl et al. |
| 5,296,518 A | 3/1994 | Grasel et al. |
| 5,393,858 A | 2/1995 | Meijs et al. |
| 5,711,960 A | 1/1998 | Shikinami |
| 6,302,916 B1 | 10/2001 | Townley et al. |
| 7,244,273 B2 | 7/2007 | Pedersen et al. |
| 7,572,295 B2 | 8/2009 | Steinberg |
| 7,611,653 B1 | 11/2009 | Elsner et al. |
| 8,632,601 B2 * | 1/2014 | Howald et al. ............ 623/22.14 |
| 2002/0143402 A1 | 10/2002 | Steinberg |
| 2003/0120347 A1 | 6/2003 | Steinberg |
| 2005/0070682 A1 * | 3/2005 | Lawrey ............................ 528/44 |
| 2005/0085915 A1 * | 4/2005 | Steinberg ............ A61B 17/1666 623/17.16 |
| 2006/0063894 A1 | 3/2006 | Alferiev et al. |
| 2006/0241758 A1 * | 10/2006 | Peterman et al. ......... 623/17.11 |
| 2007/0123991 A1 | 5/2007 | Steinberg |
| 2007/0179607 A1 | 8/2007 | Hodorek et al. |
| 2007/0224238 A1 | 9/2007 | Mansmann et al. |
| 2008/0262618 A1 | 10/2008 | Hermsen et al. |
| 2009/0088846 A1 | 4/2009 | Myung et al. |
| 2009/0118455 A1 | 5/2009 | Gunatillake et al. |
| 2009/0132047 A1 | 5/2009 | Mansmann et al. |
| 2009/0233887 A1 * | 9/2009 | Shalaby et al. ............... 514/154 |
| 2009/0240337 A1 | 9/2009 | Myung et al. |
| 2009/0259317 A1 | 10/2009 | Steinberg |
| 2010/0010114 A1 | 1/2010 | Myung et al. |
| 2010/0022479 A1 | 1/2010 | Bourban et al. |
| 2010/0023126 A1 | 1/2010 | Grotz |
| 2010/0145457 A1 | 6/2010 | Felt et al. |

FOREIGN PATENT DOCUMENTS

| | | | |
|---|---|---|---|
| FR | 1061009 * | 4/1954 | ............... A61F 2/30 |
| FR | 2803191 A1 | 7/2001 | |
| WO | 0023009 A1 | 4/2000 | |
| WO | 00053077 A3 | 9/2000 | |
| WO | 02054992 A1 | 7/2002 | |
| WO | 03047470 A2 | 6/2003 | |
| WO | 03061516 A2 | 7/2003 | |
| WO | 03061516 A3 | 7/2003 | |
| WO | 03099156 A2 | 12/2003 | |
| WO | 2003099156 A3 | 12/2003 | |

OTHER PUBLICATIONS

Thomson, T., "Polyurethanes as Specialty Chemicals", Aug. 27, 2004, pp. 1-190, Publisher: CRC Press, Published in: Boca Raton, Florida, US.

* cited by examiner

DEVICE AND METHOD FOR RESTORING JOINTS WITH ARTIFICIAL CARTILAGE

TECHNICAL FIELD

This invention relates generally to an improved method for the treatment of arthritis of joints and, more specifically, it concerns restoring a joint with an artificial cartilage.

BACKGROUND OF INVENTION

Osteoarthritis is the leading cause for joint replacement surgery worldwide. Although the bone may eventually be involved, osteoarthritis is primarily a disease of cartilage. Bones have sensory nerves just like skin. These nerves exist on the surfaces of the bone both on the femoral head and acetabulum. Normally the bone surfaces along with their sensory nerves are covered by articular cartilage or hyaline cartilage. Hyaline cartilage is unique in that not only does it not have a blood supply, it also does not possess a nerve supply, i.e., it is aneural. Therefore, as long as there is cartilage interposed between the joint surfaces, since there are no nerves, there is no pain. The pain of osteoarthritis is generated once the cartilage has eroded away, and there is resulting bone on bone contact or nerve on nerve contact.

There are three basic classifications of joints of the human body: synarthroidal, amphiarthroidal, and diarthroidal. Synarthroidal joints provide immovable articulations; amphiarthroidal joints provide mixed articulations; and diarthroidal joints provide movable articulations. Healthy fibro cartilage and hyaline cartilage within the joint provide a weight-bearing function and allow painless articulation of amphiarthroidal and diarthroidal joints.

Primary osteoarthritis is a debilitating disease that affects amphiarthroidal and diarthroidal joints. The changes that occur with primary osteoarthritis involve altered biomechanical, biochemical, histological and metabolic characteristics of the cartilage, synovial fluid and bone. Initially, these changes affect the articular cartilage and eventually affect the surrounding perichondral tissues in a cascade of events.

Articular cartilage, also called hyaline cartilage, is made of a multiphasic material with two major phases: a fluid phase composed of water (68%-85%) and electrolytes, and a solid phase composed of collagen fibrils (primarily type II collagen, 10%-20%), proteoglycans and other glycoproteins (5-10%), and chondrocytes (cartilaginous cells). 30% of all cartilage water resides in this interstitial fluid, and this amount does not vary with age. However, there is a significant increase of total amount of water in degenerating cartilages. This multiphasic system allows fluid flowing from the tissue to the solution surrounding the tissue, and vice versa, through the pores of the collage-proteoglycan solid matrix. As the fluid passes to the pores, the force exerted on the walls of the pores causes more compaction. Thus, it becomes more and more difficult to squeeze fluid from the tissue with prolonged compression. This non-linear flow-induced compression effect is very important in the physiology of cartilage not just because it determines cartilage compressive behaviors, but also because it provides the mechanism for energy dissipation.

There are many theories concerning how articular cartilage functions as a weight bearing surface, which include hydrodynamic, boundary, elastohydrodynamic and squeeze film lubrication. However, it is known that the viscoelastic properties contribute to the multiple functions of articular cartilage, including its weight bearing function. The viscoelastic properties of cartilage are due to an intricate tight meshwork of interlacing collagen fibers that physically ensnare the large macromolecules of proteoglycan.

To date, treatment of osteoarthritis has been with the use of total joint replacement surgery. This entails resection of the proximal femur (femoral head and neck), reaming of the femoral intramedullary canal and the insertion of one or more modular artificial metal component(s) to replace the diseased cartilage on the resected bone. Similarly the acetabulum is removed by reaming the socket down to bleeding bone and the impacting of an artificial socket into the pelvis. The two components are then joined by suturing the dissected surrounding tissues together, joining the two components into contact with each other. The materials used for these devices are usually an alloy of various metals typically cobalt, chrome and titanium. The bearing surfaces vary from polyethylene on metal, metal on metal, ceramic on ceramic, and various combinations of them all. The operations are extensive dissections with implantation of large quantities of inert material into the human body. Potential complications are extensive and can range anywhere from minor wound complications to death of the patient. All approaches entail the complete replacement and substitution of the joint with artificial components with their own inherent mechanics of joint function. It would be desirable to provide a method and apparatus for treating osteoarthritis that minimizes surgical intervention and human tissue resection and substitution.

SUMMARY OF INVENTION

A primary object of the present invention is to provide an intra-articular device as both a substitute for degenerated cartilage and enhancement for the remaining cartilage of an arthritic joint, so as to minimize surgical intervention and human tissue resection and substitution.

A specific object is to provide an intra-articular device that fits snugly and easily over the existing femoral head of a hip bone without the need for tissue resection of either the femoral head or acetabulum. It should be simple and easy to insert and economical in cost to manufacture. It should be designed so that it is not degraded or fractured and does not displace or dislocate after insertion.

A further object is to provide an interpositional joint membrane that does not irritate the articulating and surrounding tissues and provide an articulating surface with a coefficient of friction similar to human hyaline cartilage.

An additional object is to provide a cartilage enhancing device that will utilize the body's own joint fluid (synovial fluid) to re-establish the viscoelastic properties of the joint surface.

Another primary object of the invention is to provide an improved method of reconstructing an arthritic joint through minimally invasive techniques and minimal, if any, human tissue resection and elimination. In particular, it is desired to utilize the body's own tissues and fluids in the restoration of joint function and pain elimination.

In accordance with the present invention, an intra-articular device comprises a membrane shaped like a cap having a peripheral geometry similar to that of a head of a bone for a joint to be restored and an open end sized to be applied over the bone proximate the head, so that the open end can be stretched over the head of the bone and held in position on the bone interposed between the head and its corresponding articular component of the joint, wherein said membrane is made of a material selected to have a property of absorbing the joint's own synovial fluid to thereby cause the membrane to swell and have a viscoelastic property similar to the body's own articular hyaline cartilage.

In a preferred embodiment, the intra-articular device is adapted for use on a femoral head of a femoral bone for a hip joint. The device has a balloon shape corresponding to the geometry of the femoral head, and the diameter of its open end is smaller than the balloon shape of the device. Because of the elastic quality of the device material and its shape, the device can be stretched over the femoral head like a condom and secured in place by the open end reverting to its original resting diameter thereby fitting snugly and securely over the femoral head and neck.

A class of hydro-swellable polyether-urethane-urea material is particularly suitable for absorbing the joint's own synovial fluid to thereby cause the membrane to swell and have a viscoelastic property similar to the body's own articular hyaline cartilage. The preferred polyether-urethane (PEU) and polyether-urethane-urea (PEUU) elastomer materials undergo swelling when placed in the biological environment of at least 30% increase in volume by virtue of having a highly hydrophilic polyalkylene oxide as an inherent part of their segmented chain molecules. In particular, a hydroswellable, segmented, aliphatic polyurethane-urea comprising polyoxyalkylene chains covalently interlinked with polyalkylene urethane chain segments, which are further interlinked with aliphatic urea chain segments, exhibits at least 50% increase in volume when placed in the biological environment. The intra-articular device can be made from a viscoelastic polyether-urethane-urea material by dip molding.

A related method of installing an intra-articular device as artificial cartilage in a joint to be restored comprises forming a membrane cap having a shape corresponding to the peripheral geometry of a head of a bone for a joint to be restored and an open end sized to be applied over the head of the bone, surgically exposing the head of the bone, installing the membrane cap over the head of the bone, then repositioning the capped head of the bone back in its place in the joint with the membrane interposed between the head of the bone and its corresponding articular component of the joint. Any remaining articular cartilage of the joint is placed in direct contact with the membrane forming a cartilage-membrane-cartilage construct. Since this construct is intra-articular, it is therefore immersed in the joint's synovial fluid. Due to its unique ("hydro-swellable") properties, the membrane material absorbs the joint synovial fluid within minutes and can begin to function as a dynamic cartilage substitute in concert with the remaining joint cartilage and synovial fluid. As pressure is applied to the "capped" head of the bone, the synovial fluid is expressed from the device at the point of contact, and then as that weight or force is removed the synovial fluid is reabsorbed in the membrane. This non-linear flow-induced compression effect recreates the cartilage viscoelastic behavior as well as provides for energy dissipation. The combined effect of the device with the body's own remaining articular cartilage and synovial fluid will eliminate joint pain and restore joint function with minimal tissue dissection, resection and complications.

Besides hip joints, the method of installing a membrane device as artificial cartilage can be used more generally for restoring the function of other types of diseased or defective articulating joints in humans. For example, a membrane device can be adapted for use for restoring a knee joint. A membrane device can also be adapted for use for restoring joints in animals.

Other objects, features, and advantages of the present invention will be explained in the following detailed description of the invention having reference to the appended drawings.

DETAILED DESCRIPTION OF INVENTION

In the following detailed description of the invention, certain preferred embodiments are described providing certain specific details of their implementation. However, it will be recognized by one skilled in the art that many other variations and modifications may be made given the disclosed principles of the invention.

Figure 1:
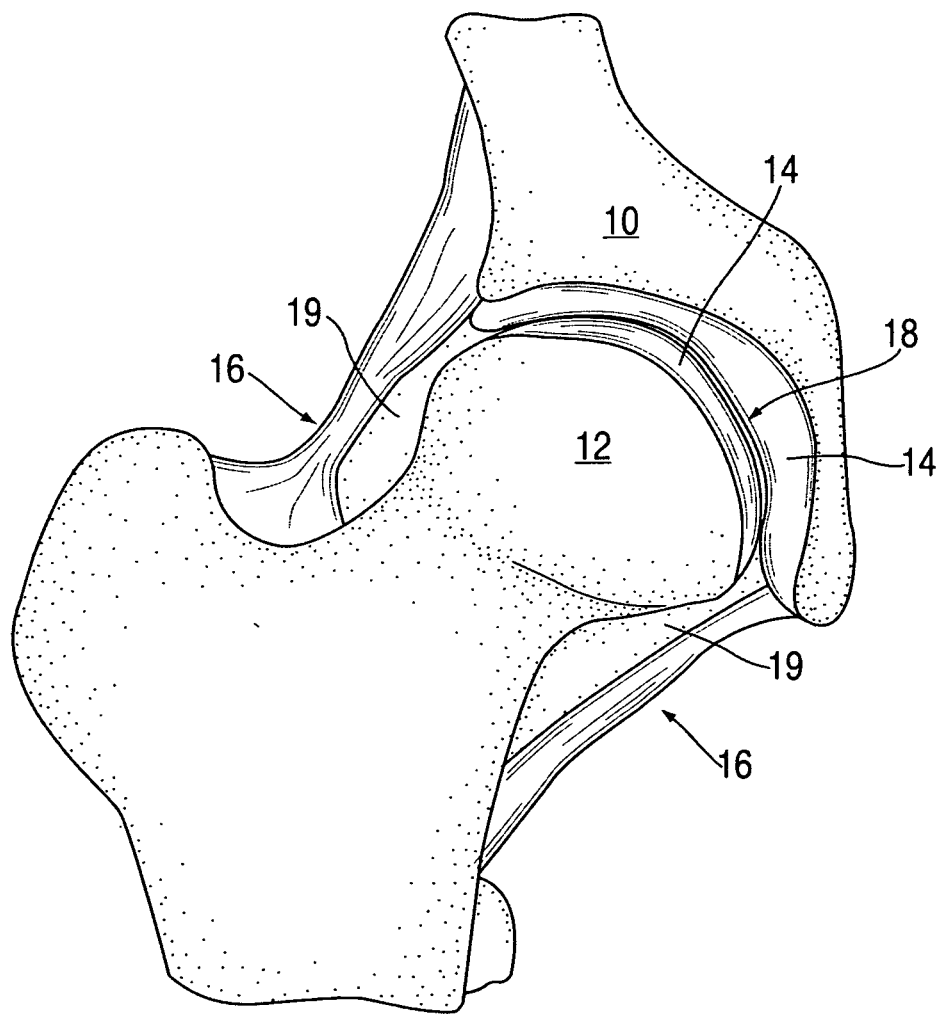
FIG. 1 is a cross sectional view illustrating a normal hip joint depicting the femoral head (hip bone), the acetabulum (socket), and the joint capsule.

In FIG. 1, a normal hip joint is shown in cross sectional view with the femoral head 12 of the hip bone positioned in the acetabulum 10 of the hip joint socket with respective layers of articular cartilage 14 forming a smooth joint surface 18 with cartilage-on-cartilage contact. The joint capsule 16 completely encapsulates the hip joint and is filled with synovial fluid 19 that flows to the articular cartilage surfaces 18 of both the femoral head 12 and the acetabulum 10.

Figure 2:
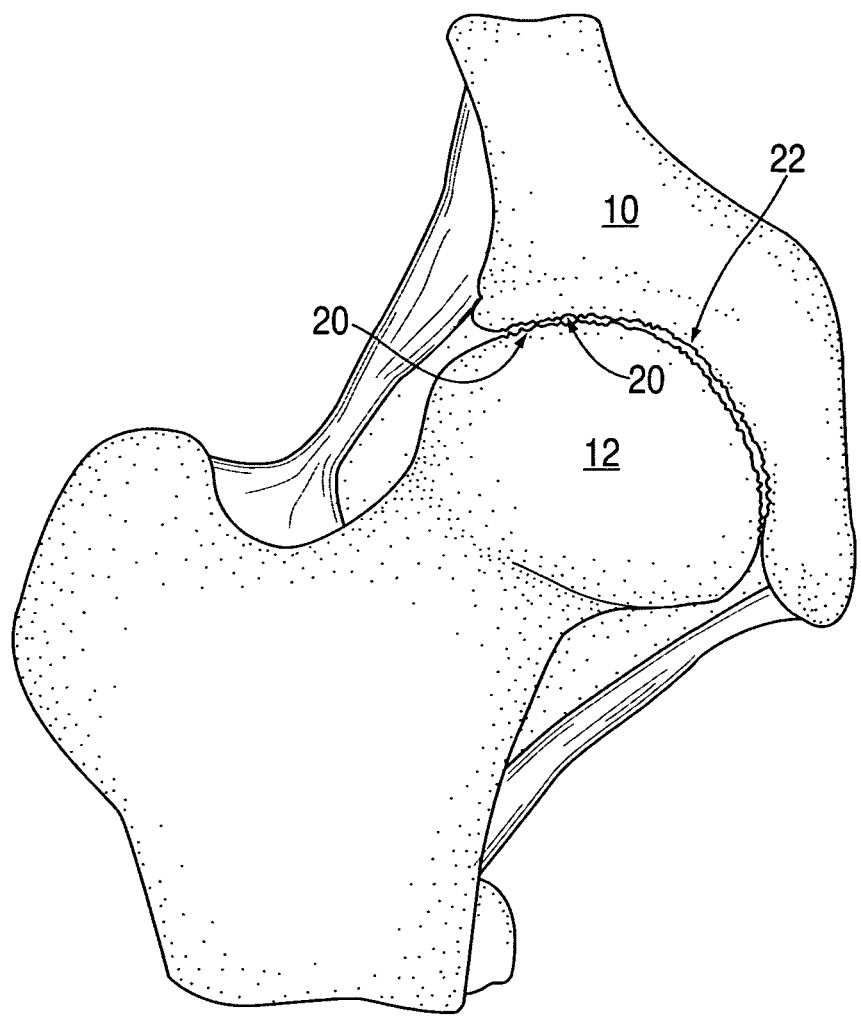
FIG. 2 is a cross sectional view of an arthritic hip joint illustrating the loss of cartilage surface from both the femoral head and acetabulum.

In FIG. 2, an arthritic hip joint is shown in cross sectional view having the articular cartilage of the femoral head 12 and acetabulum 10 worn down on the respective surfaces 20 so that there is raw bone-on-bone contact. This results in contact between the roughened joint surfaces 20 that causes pain. The joint space is greatly reduced due to the lack of cartilage.

Figure 3:
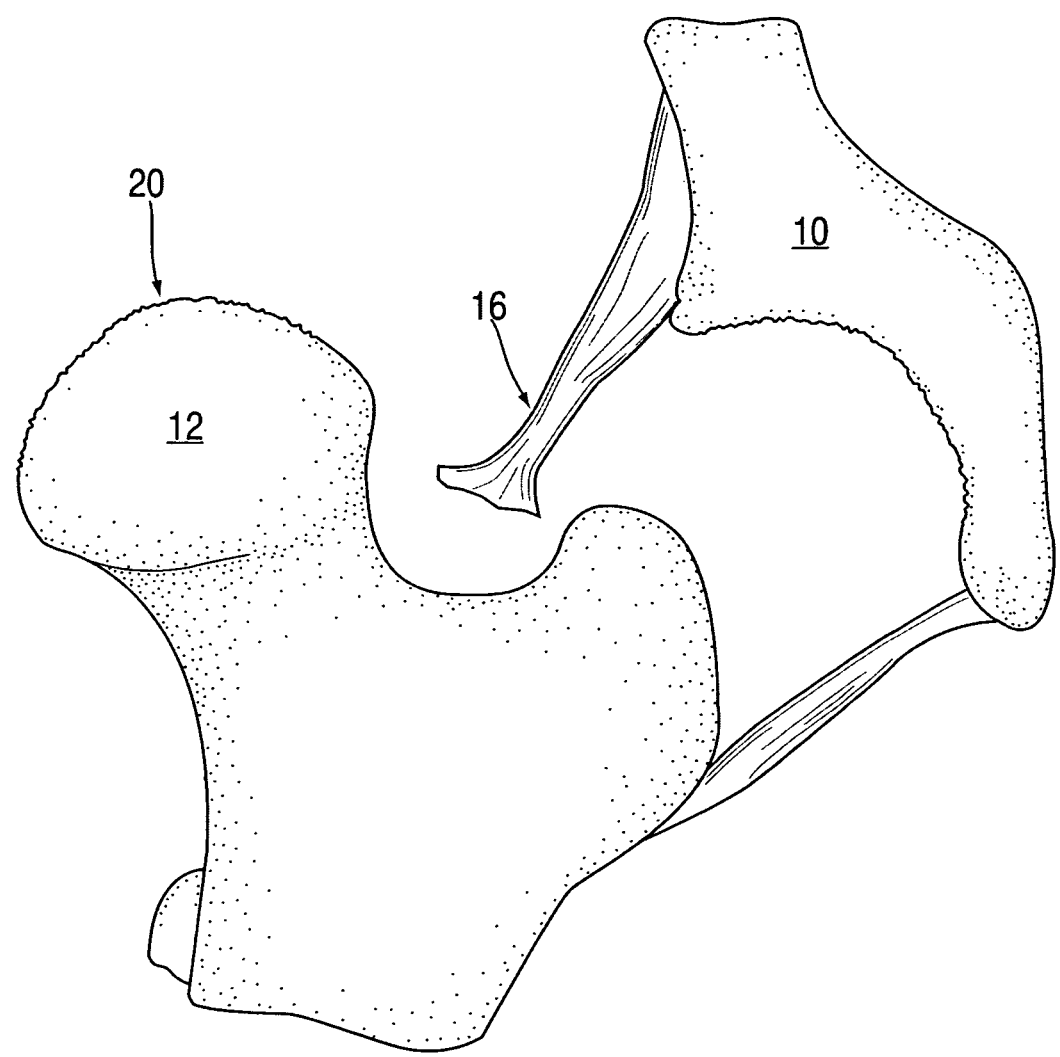
FIG. 3 is a cross sectional view showing the femoral head of an arthritic hip that is surgically dislocated from the hip socket and joint capsule for installation of the membrane device.

In FIG. 3, a surgical procedure for restoring the arthritic hip in accordance with the present invention temporarily removes (dislocates) the femoral head 12 of the hip bone from the acetabulum 10 outside the joint capsule 16 (by detaching one side) so that the head 12 can be accessed.

Figure 4:
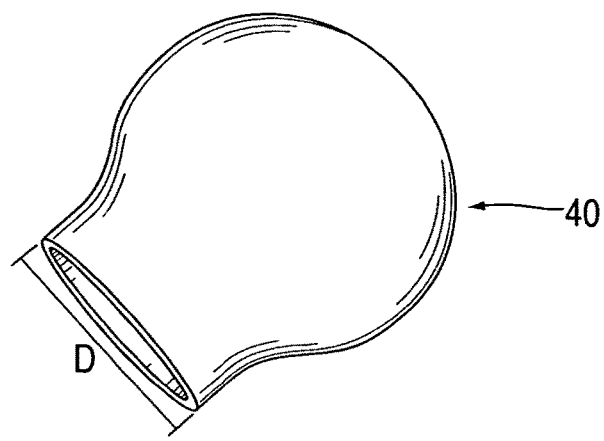
FIG. 4 shows a preferred embodiment of the membrane device for placement over the femoral head.

In FIG. 4, a preferred embodiment of an intra-articular membrane device 40 for placement over the femoral head is illustrated. The intra-articular membrane device 40 has a balloon shape corresponding to the geometry of the femoral head, and the diameter D of its open end is sized to be approximately equal to the diameter of the bone proximate the head and smaller than the balloon shape of the device. Because of the elastic quality of the device material and its shape, the device can be stretched over the femoral head like a condom and secured in place by the open end reverting to its original resting diameter D thereby fitting snugly and securely over the femoral head and neck.

The membrane device is made of a material selected to have a property of absorbing the joint's own synovial fluid to thereby cause the membrane to swell and have a viscoelastic property similar to the body's own articular hyaline cartilage. A class of hydro-swellable polyether-urethane-urea material is found to be particularly suitable for this purpose, as described in U.S. Provisional Application Ser. No. 61/069,046 filed on Mar. 12, 2008, in the name of Shalaby W. Shalaby, the disclosure of which is incorporated herein by reference.

The preferred polyether-urethane (PEU) and polyether-urethane-urea (PEUU) elastomer materials undergo swelling when placed in the biological environment of at least 30% increase in volume by virtue of having a highly hydrophilic polyalkylene oxide as an inherent part of their segmented chain molecules. In particular, a hydroswellable, segmented, aliphatic polyurethane-urea comprising polyoxyalkylene chains covalently interlinked with polyalkylene urethane chain segments, which are further interlinked with aliphatic urea chain segments, exhibits at least 50% increase in volume when placed in the biological environment. The PEUU materials were tested and found to have 60% to 91% increase in volume after immersion in 1% methyl cellulose solution (to simulate synovial fluid viscosity) for 15 hours at 37° C.

The polyalkylene glycol chains can comprise at least one type of oxyalkylene sequences selected from the group represented by oxyethylene, oxypropylene, oxytrimethylene, and oxytetramethylene repeat units and the urethane chain segments are derived from at least one diisocyanate selected from the group represented by hexamethylene diisocyanate, hexamethylene diisocyanate, octamethylene diisocyanate, decamethylene diisocyanate, dodecamethylene diisocyanate, 1,4 cyclohexane diisocyanate, lysine-derived diisocyanate, and cyclohexane bis(methylene isocyanate). The resulting polyoxyalkylene urethane molecules can have at least one isocyanate terminal group are chain-extended with an alkylene diamine selected from the group represented by ethylene-, trimethylene, tetramethylene-, hexamethylene-, and octamethylene-diamine, thus forming polyetherurethane-urea segmented chains.

The preferred polyether-urethane (PEU) and polyether-urethane-urea (PEUU) elastomer materials are suitable for use as artificial cartilage for restoring the function of diseased or defective articulating joints in humans and animals. A membrane cap corresponding to the peripheral geometery of a joint can be formed by dip molding and thermosetting the material on a mold form. The membrane cap can then be installed on the joint in a surgical procedure as described above for a hip joint.

Figure 5:
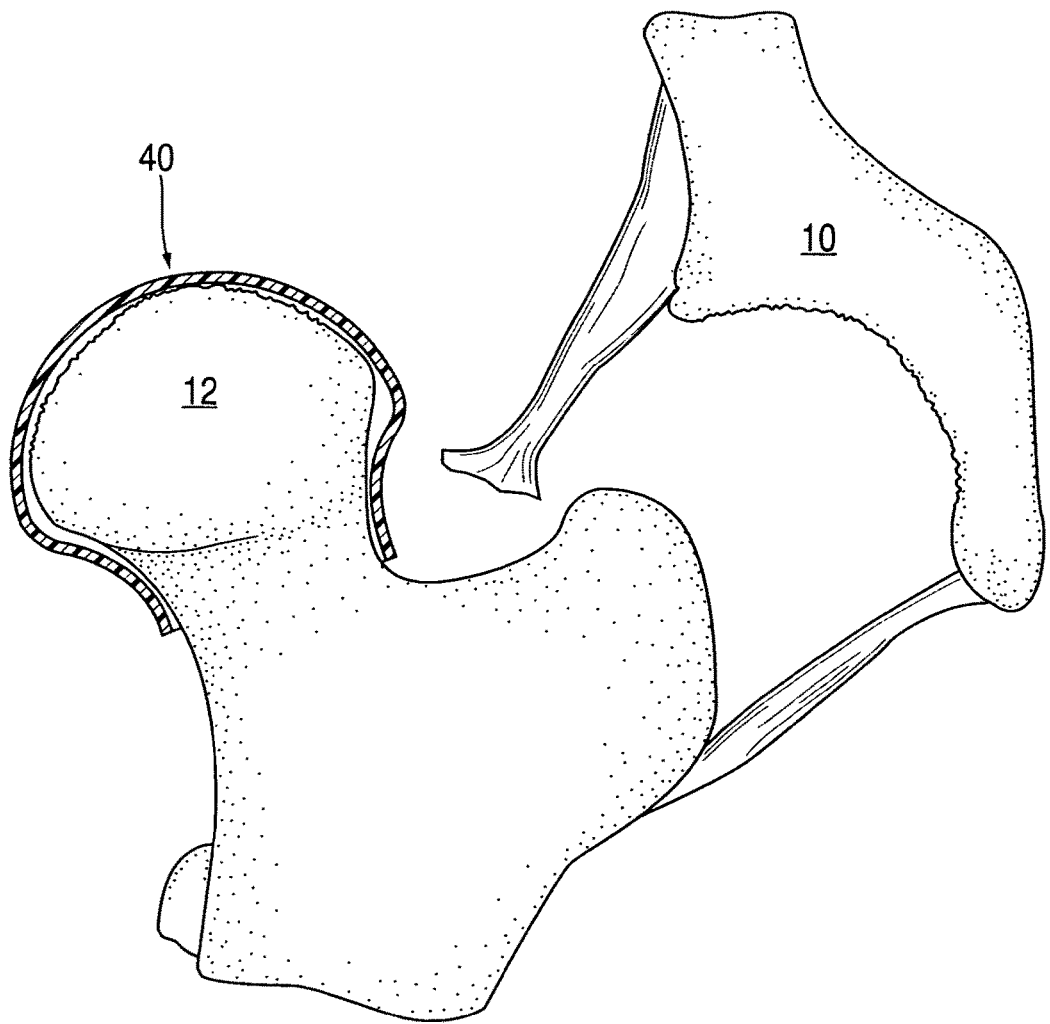
FIG. 5 shows the membrane device slipped over the arthritic femoral head.
Figure 6:
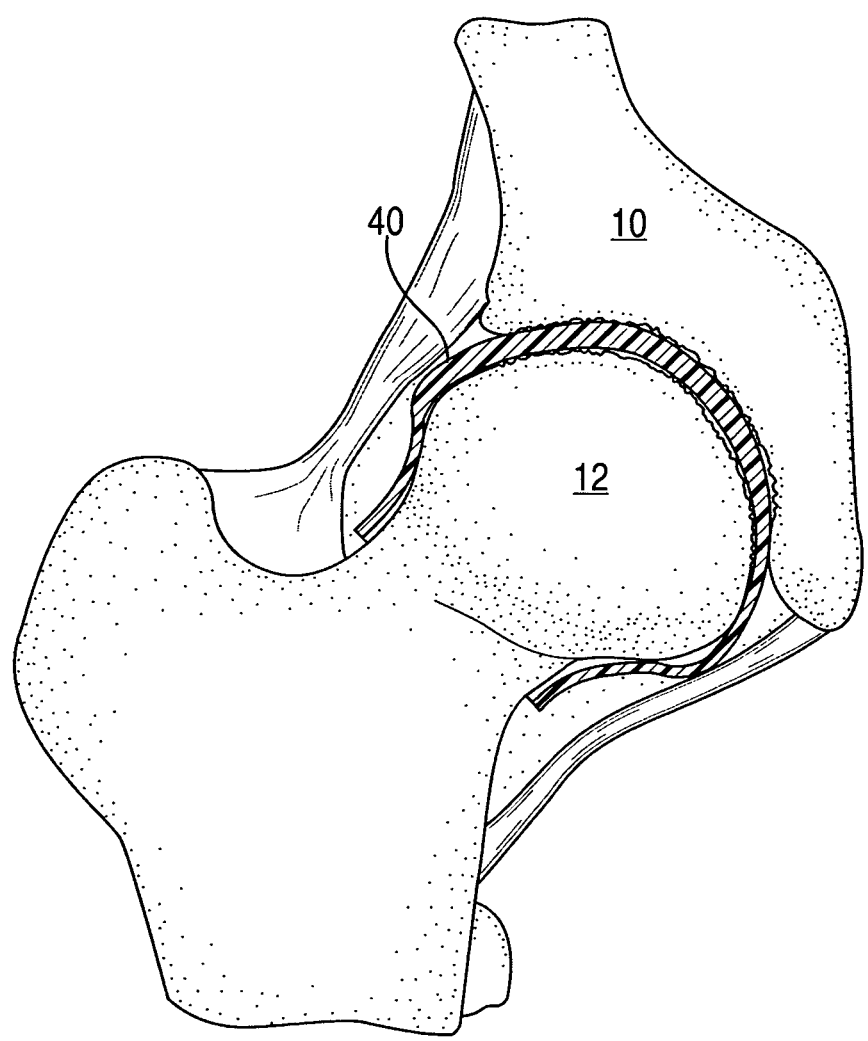
FIG. 6 shows the restored arthritic hip with the membrane device over the femoral head swollen with synovial fluid to re-establish the joint space and a smooth joint surface.

In FIG. 5, the intra-articular membrane device 40 is shown placed over the femoral head 12 of the hip bone. FIG. 6 shows the restored arthritic hip with the membrane device 40 applied over the femoral head 12 become swollen with synovial fluid to interpose a layer of artificial cartilage and re-establish the joint space and a smooth joint surface.

Besides hip joints, the method of installing a membrane device as artificial cartilage can be used more generally for restoring the function of other types of diseased or defective articulating joints in humans. For example, a membrane device can be adapted for use for restoring a knee joint. A membrane device can also be adapted for use for restoring joints in animals.

It is understood that many modifications and variations may be devised given the above description of the principles of the invention. It is intended that all such modifications and variations be considered as within the spirit and scope of this invention, as defined in the following claims.

The invention claimed is:

1. An intra-articular device comprising:
a membrane shaped like a cap having a peripheral geometry similar to that of a substantially unmodified head of a bone for a joint to be restored, a cylindrical neck, and an open end of the cylindrical neck sized to be applied over the bone proximate the head, so that the open end can be stretched over the head and neck of the bone and held in position on the bone with the membrane interposed between the head and its corresponding articular component of the joint, wherein said membrane is made of a material selected to have a property of absorbing the joint's own synovial fluid to thereby cause the membrane to swell and have a viscoelastic property similar to the body's own articular hyaline cartilage, wherein the membrane is adapted for use on a femoral head of a femoral bone for a hip joint, wherein said membrane has a balloon shape corresponding to the geometry of the femoral head, and the diameter of its open end of its cylindrical neck is smaller than the balloon shape of the device, and wherein the membrane is made of a polyether-urethane material.

2. An intra-articular device according to claim 1, wherein the membrane is formed by dip molding.